US012414866B2

(12) United States Patent
Liao et al.

(10) Patent No.: US 12,414,866 B2
(45) Date of Patent: Sep. 16, 2025

(54) SMART KNEE JOINT FOR A HUMAN LOWER LIMB EXOSKELETON, A PROSTHESIS AND AN ORTHOSIS

(71) Applicant: The Chinese University of Hong Kong, Hong Kong (CN)

(72) Inventors: Wei-Hsin Liao, Hong Kong (CN); Fei Gao, Neijiang (CN)

(73) Assignee: The Chinese University of Hong Kong, Hong Kong (CN)

( * ) Notice: Subject to any disclaimer, the term of this patent is extended or adjusted under 35 U.S.C. 154(b) by 771 days.

(21) Appl. No.: 17/453,600

(22) Filed: Nov. 4, 2021

(65) Prior Publication Data

US 2023/0025654 A1     Jan. 26, 2023

(30) Foreign Application Priority Data

Jul. 21, 2021   (CN) .......................... 202110834335.3

(51) Int. Cl.
   *A61F 2/64*     (2006.01)
   *A61B 5/107*    (2006.01)
   (Continued)

(52) U.S. Cl.
   CPC .............. *A61F 2/64* (2013.01); *A61B 5/1071* (2013.01); *A61F 2/68* (2013.01); *A61F 2/74* (2021.08);
   (Continued)

(58) Field of Classification Search
   None
   See application file for complete search history.

(56) References Cited

U.S. PATENT DOCUMENTS

| 5,062,856 A | 11/1991 | Sawamura et al. |
| 5,250,050 A | 10/1993 | Poggie et al. |
| (Continued) | | |

FOREIGN PATENT DOCUMENTS

| CN | 107874875 | 4/2018 | |
| CN | 111481402 A | * 8/2020 | ........... A61B 5/1038 |

OTHER PUBLICATIONS

"Chinese Application Serial No. 202110834335.3 Office Action mailed on Apr. 12, 2025", with English translation 22 pgs.

*Primary Examiner* — David H Willse
(74) *Attorney, Agent, or Firm* — Schwegman Lundberg & Woessner, P.A.

(57) ABSTRACT

The present application relates to a smart knee joint for a human lower limb exoskeleton, a prosthesis, and an orthosis. The smart knee joint reproduces part or all of the biomechanics of the knee joint of the human body by using a motor driving unit and a controllable elastic energy storage unit based on a magnetorheological damper. The motor driving unit here can be replaced with a controllable damping unit. The smart knee joint is developed for helping amputees or patients with impaired mobility regain/repair natural gaits and also reduce their burden of walking. The motor drive unit operates in a generator mode and an actuator mode. Energy harvesting technologies are exploited to reduce the power consumption of the smart knee joint then to prolong the working time. In addition, the controllable elastic energy storage unit based on the magnetorheological damper can further reduce the energy consumption of the smart knee joint, and also simplify the control of the knee joint.

23 Claims, 13 Drawing Sheets

(51) Int. Cl.
*A61F 2/68* (2006.01)
*A61F 2/70* (2006.01)
*A61F 2/74* (2006.01)
*A61F 5/01* (2006.01)
*B25J 9/00* (2006.01)
*A61F 2/50* (2006.01)
*A61F 2/76* (2006.01)

(52) U.S. Cl.
CPC ............ *A61F 2/748* (2021.08); *A61F 5/0123* (2013.01); *B25J 9/0006* (2013.01); *A61B 2562/0219* (2013.01); *A61F 2002/5003* (2013.01); *A61F 2002/5004* (2013.01); *A61F 2002/5006* (2013.01); *A61F 2002/5073* (2013.01); *A61F 2002/5079* (2013.01); *A61F 2002/6818* (2013.01); *A61F 2002/6836* (2013.01); *A61F 2002/6845* (2013.01); *A61F 2002/6854* (2013.01); *A61F 2002/701* (2013.01); *A61F 2002/704* (2013.01); *A61F 2002/7615* (2013.01); *A61F 2005/0155* (2013.01); *A61F 2005/0169* (2013.01); *A61F 2005/0179* (2013.01)

(56) References Cited

U.S. PATENT DOCUMENTS

| | | |
|---|---|---|
| 5,571,205 A | 11/1996 | James |
| 6,206,933 B1 | 3/2001 | Shorter et al. |
| 6,423,098 B1 | 7/2002 | Biedermann |
| 6,517,585 B1 | 2/2003 | Zahedi et al. |
| 6,610,101 B2 | 8/2003 | Herr et al. |
| 6,719,806 B1 | 4/2004 | Zahedi et al. |
| 6,755,870 B1 | 6/2004 | Biedermann et al. |
| 6,764,520 B2 | 7/2004 | Deffenbaugh et al. |
| 6,905,513 B1 | 6/2005 | Metzger |
| 6,911,050 B2 | 6/2005 | Molino et al. |
| 7,101,487 B2 | 9/2006 | Hsu et al. |
| 7,279,009 B2 | 10/2007 | Herr et al. |
| 7,279,010 B2 | 10/2007 | Cheng |
| 7,314,490 B2 | 1/2008 | Bédard et al. |
| 7,485,152 B2 | 2/2009 | Haynes et al. |
| 7,582,119 B2 | 9/2009 | Chen |
| 7,588,604 B2 | 9/2009 | Okuda et al. |
| 7,597,716 B2 | 10/2009 | Grafinger |
| 7,833,285 B2 | 11/2010 | Reinhardt |
| 7,883,548 B2 | 2/2011 | Lang |
| 7,942,935 B2 | 5/2011 | Iversen et al. |
| 7,981,164 B1 | 7/2011 | Schultz |
| RE42,903 E | 11/2011 | Deffenbaugh et al. |
| 8,231,687 B2 | 7/2012 | Bédard et al. |
| 8,231,688 B2 | 7/2012 | Fairbanks et al. |
| 8,343,227 B2 | 1/2013 | Metzger et al. |
| 8,403,997 B2 | 3/2013 | Sykes et al. |
| 8,444,704 B2 | 5/2013 | Palmer et al. |
| 8,500,818 B2 | 8/2013 | Metzger et al. |
| 8,617,254 B2 | 12/2013 | Bisbee, Iii et al. |
| 8,764,849 B2 | 7/2014 | Omarsson et al. |
| 8,870,969 B2 | 10/2014 | Chabloz |
| 8,920,517 B2 | 12/2014 | Smith et al. |
| 9,149,371 B2 | 10/2015 | Karlsson et al. |
| 9,345,591 B2 | 5/2016 | Bisbee, Iii et al. |
| 9,730,814 B2 | 8/2017 | Omarsson et al. |
| 9,737,419 B2 | 8/2017 | Herr et al. |
| 9,757,253 B2 | 9/2017 | Dressler et al. |
| 9,770,346 B2 | 9/2017 | Karlsson et al. |
| 9,775,715 B2 | 10/2017 | Boiten |
| 9,844,448 B2 | 12/2017 | Karlsson et al. |
| 9,901,466 B2 | 2/2018 | Duger et al. |
| 9,987,152 B2 | 6/2018 | Chabloz et al. |
| 10,034,781 B2 | 7/2018 | Shen |
| 10,039,652 B2 | 8/2018 | Zahedi et al. |
| 10,231,850 B2 | 3/2019 | Shen |
| 10,251,761 B2 | 4/2019 | Boiten |
| 10,285,827 B2 | 5/2019 | Zahedi et al. |
| 10,413,430 B2 | 9/2019 | Dressler et al. |
| 10,548,746 B2 | 2/2020 | Blanc |
| 10,610,383 B2 | 4/2020 | Pelisson et al. |
| 10,765,537 B2 | 9/2020 | Smith et al. |
| 2004/0186591 A1 | 9/2004 | Lang |
| 2005/0154473 A1 | 7/2005 | Bassett |
| 2005/0283257 A1 | 12/2005 | Bisbee et al. |
| 2006/0136072 A1 | 6/2006 | Bisbee et al. |
| 2006/0293761 A1 | 12/2006 | Baumann et al. |
| 2007/0083272 A1 | 4/2007 | Van et al. |
| 2010/0292807 A1 | 11/2010 | Velez et al. |
| 2012/0259431 A1 | 10/2012 | Han et al. |
| 2013/0035769 A1 | 2/2013 | Bédard et al. |
| 2013/0173019 A1 | 7/2013 | Sykes et al. |
| 2015/0018972 A1 | 1/2015 | Albrecht-Laatsch |
| 2015/0342759 A1 | 12/2015 | Hellberg et al. |
| 2016/0367385 A1 | 12/2016 | Hashimoto et al. |
| 2017/0250632 A1 | 8/2017 | Herr et al. |
| 2017/0360580 A1 | 12/2017 | Karlsson et al. |
| 2018/0036150 A1 | 2/2018 | Smit et al. |
| 2018/0200082 A1 | 7/2018 | Auberger et al. |
| 2018/0289514 A1 | 10/2018 | Chabloz et al. |
| 2019/0231560 A1 | 8/2019 | Boiten |
| 2019/0358061 A1 | 11/2019 | Zahedi et al. |
| 2019/0380847 A1 | 12/2019 | Kampas et al. |
| 2020/0054465 A1 | 2/2020 | Velez et al. |
| 2020/0188138 A1 | 6/2020 | Arelekatti et al. |
| 2022/0176547 A1* | 6/2022 | Smith .................. A61H 1/0255 |

* cited by examiner

SMART KNEE JOINT FOR A HUMAN LOWER LIMB EXOSKELETON, A PROSTHESIS AND AN ORTHOSIS

CLAIM FOR PRIORITY

This application claims the benefit of priority of Chinese Application Serial No. 202110834335.3, filed Jul. 21, 2021, which is hereby incorporated by reference in its entirety.

TECHNICAL FIELD

The present application relates to a smart knee joint, and particularly, to a smart knee joint for a human lower limb exoskeleton, a prosthesis, and an orthosis. In addition, the present application relates to a method of assisting a knee joint.

BACKGROUND

With the rapid development of the economy, people's living standards gradually improve, and the attention from society to the disabled increases over time. Due to the loss of motor function, the self-care ability of the disabled decreases, resulting in a greatly reduced sense of happiness and self-recognition of life. Currently, research institutes and companies have proposed several lower limb prostheses, exoskeletons, and orthopedic devices to help individuals with lower limb amputation or stroke hemiplegia recover part or all of their locomotion functions. These human motion assistive devices can help a wearer regain or repair walking functions through actively or passively reproducing biomechanical features of the corresponding joint, such as moment-angle curve, or angle tracking.

Exoskeletons for lower limbs have received extensive attention from the research and industrial fields, and researchers have proposed a variety of active and passive exoskeletons for lower limbs. Such devices have been employed to assist the paraplegias to stand up and walk independently so that these patients do not rely on wheelchairs. Besides, lower limb exoskeletons are also designed for improving the weight-bearing capacity of soldiers. In addition, prostheses have been developed for helping amputees to regain locomotion function by mimicking the function of the amputated lower limb joints. The conventional passive prostheses are lightweight and low-cost. However, as the mechanical characteristics are fixed, these passive prostheses cannot precisely reproduce the required function, which results into clinical problems such as poor gait adaptability, asymmetric gait, and obvious increase of metabolism of the wearer.

In order to overcome the drawbacks of conventional passive prostheses, researchers proposed powered prostheses that utilize drivers, controllers, sensors, and power supplies to actively adjust the dynamics of the prostheses thereby mimicking the function of the corresponding human lower limb joints. Clinical trials have shown that power lower limb prostheses can greatly improve the walking gait of amputees and reduce their burden of walking, compared to traditional passive prostheses.

However, for powered assistive devices, actuators and power supplies that could meet the function requirements still face enormous challenges due to the limitations of current technologies. The commercially available actuators, such as DC motors, do not have a high power-to-weight ratio. With a limited size and weight, the DC motors are hard to provide the required driving force or torque.

In addition, due to the limitation of the energy density of the lithium battery, the energy consumption of the mobile device is one of the main issues that should be considered in the development of the mobile device.

Smart actuators based on smart materials have their own advantages, such as magnetorheological (MR) dampers/magnetorheological rotary brakes. Smart actuators possess lower energy consumption when mimicking the mechanical properties of the corresponding joints, compared with DC motors. Because of that, the batteries for powering these smart actuators can be downsized, and the working time for one full charging can be prolonged. In addition, smart actuators can be simply controlled to provide a controllable damping force/torque. Given that, it is expected that smart actuators will be widely used in assistive devices due to their merits.

Therefore, it is of great significance to develop a smart knee joint utilizing a smart actuator to improve the performance of lower limb exoskeletons, prostheses, and orthoses.

SUMMARY OF INVENTION

In order to overcome the challenges in actuators, power supplies, and control of knee joints in lower limb exoskeletons, prostheses, and orthopedic devices, the present application proposes a smart knee joint utilizing energy harvesting technologies, elastic components for storing energy, and smart actuators. The smart knee joint can reproduce part or all of the biomechanics of the human knee joint while having low power consumption. In addition, the smart knee joint employs a novel mechanical design to simplify the control of the device.

According to one aspect of the present application, here this invention discloses a smart knee joint for a human lower limb exoskeleton, a prosthesis, or an orthosis. The smart knee joint is attached to the knee joint and may include:
1) a motor driving unit or a controllable damping unit, the motor driving unit includes a motor and a transmission, the motor driving unit has two working modes: a generator mode and an actuator mode, and the working mode of the motor driving unit is adjusted based on the states and walking modes of the knee joint;
2) an elastic energy storage unit including an elastic element, a transmission, and a working mode regulator, the elastic energy storage unit has three working modes: being locked, free mode, and energy dissipation mode, the working mode of the elastic energy storage unit is adjustable based on the states and walking modes of the knee joint;
3) sensors for detecting the motion of the knee joint;
4) a controller for monitoring the states and walking modes of the knee joint in real-time based on signals of the sensors, and then generating control signals for the elastic energy storage unit and the motor driving unit or the controllable damping unit;
5) a power supply for powering the motor driving unit, the controllable damping unit, the elastic energy storage unit, the sensors, and the controller, as well as for storing the electric energy recovered by the motor, the power supply is one or both of a battery and a supercapacitor; and
6) connecting devices, comprising a thigh connecting device and a shank connecting device.

According to an example embodiment of the present application, the motor drive unit comprises a motor, a gear reduction box, and a bevel gear transmission.

According to an example embodiment of the present application, the motor drive unit comprises a motor and a harmonic gear transmission.

According to an example embodiment of the present application, the motor drive unit comprises a motor, a gear transmission, a ball-screw transmission, and a slider-crank mechanism.

According to an example embodiment of the present application, the motor drive unit comprises a motor, a timing-belt transmission, a ball-screw transmission, and a slider-crank mechanism.

According to an example embodiment of the present application, the elastic energy storage unit is configured in parallel with the motor drive unit.

According to an example embodiment of the present application, for the elastic energy storage unit, the elastic component, the transmission, and the working mode regulator are configured in series.

According to an example embodiment of the present application, the elastic component in the elastic energy storage unit is one or more of a coil spring, a leaf spring, a gas spring, and a rubber spring.

According to an example embodiment of the present application, the transmission in the elastic energy storage unit is one or more of a pulley rope mechanism, a slider-crank mechanism, and a cam mechanism.

According to an example embodiment of the present application, a specified cam profile is generated to enable the elastic energy storage unit to reproduce a torque-angle curve.

According to an example embodiment of the present application, the working mode regulator in the elastic energy storage unit comprises a motor, and a ball-screw drive or a screw drive.

According to an example embodiment of the present application, when the elastic energy storage unit operates in being locked mode, the elastic component is compressed or stretched to store energy, and the motor in the working mode regulator is powered to hold the elastic component and maintain an unchanged position.

According to an example embodiment of the present application, when the elastic energy storage unit operates in the free mode, the motor in the working mode regulator is powered off and can be freely rotated.

According to an example embodiment of the present application, when the elastic energy storage unit operates in the energy dissipation mode, the motor in the working mode regulator is powered to provide a controllable damping torque.

According to an example embodiment of the present application, the motor works as a generator to recover electrical energy.

According to an example embodiment of the present application, the working mode regulator comprises a clutch, a gear transmission, a ball-screw transmission, and a restoring spring.

According to an example embodiment of the present application, the clutch engages in the event of a power failure or energization.

According to an example embodiment of the present application, when the elastic energy storage unit is in being locked mode, the clutch in the working mode regulator is energized or de-energized to engage, and the ball-screw transmission in the working mode regulator is locked.

According to an example embodiment of the present application, when the elastic energy storage unit is in a free mode, the clutch in the mode regulator is energized or de-energized to be fully disengaged, and the ball-screw transmission in the working mode regulator moves freely.

According to an example embodiment of the present application, when the elastic energy storage unit operates in energy dissipation mode, the clutch is not fully engaged, and the frictional force of the clutch is controlled by adjusting the energized current to dissipate mechanical energy.

According to an example embodiment of the present application, the working mode regulator comprises a magnetorheological (MR) damper and a restoring spring.

According to an example embodiment of the present application, when the elastic energy storage unit is in the being locked mode, the magnetorheological damper in the working mode regulator is energized and the magnetorheological damper is locked.

According to an example embodiment of the present application, the magnetorheological damper in the working mode regulator is de-energized when the elastic energy storage unit is operable in the free mode.

According to an example embodiment of the present application, when the elastic energy storage unit operates in the energy dissipation mode, the magnetorheological damper in the working mode regulator is energized, and the damping force of the magnetorheological damper is adjusted by adjusting the energizing current of the magnetorheological damper, and there is a relative motion between the piston of the magnetorheological damper and the housing of the magnetorheological damper.

According to an example embodiment of the present application, the working mode regulator comprises a hydraulic cylinder, a hydraulic valve, and a restoring spring, and the working mode of the elastic energy storage unit is regulated by controlling the hydraulic valve.

According to an example embodiment of the present application, the sensors comprise one or more of an axial force sensor, a moment sensor, a knee angle sensor, an inertial measurement unit (IMU) for measuring the motion of the thigh, an IMU for measuring the motion of the shank, and electromyographic signal sensors.

According to an example embodiment of the present application, the controller detects the states and walking modes of the knee joint based on signals of the sensors and generates one or both of a reference angle or a reference moment for the motor drive unit.

According to an example embodiment of the present application, by controlling the motor drive unit, the controllable damping unit, and the elastic energy storage unit, the knee joint can reproduce the biomechanical features of the human knee joint completely or partially.

According to an example embodiment of the present application, the biomechanical features of the human knee joint are torque-angle curve during the stance phase and angle tracking features during the swing phase.

According to an example embodiment of the present application, the controllable damping unit is a magnetorheological rotary brake that can adjust the impedance of the controllable damping unit by controlling the current of the magnetorheological rotary brake.

According to an example embodiment of the present application, the controllable damping unit comprises a magnetorheological damper and a slider-crank mechanism, and the magnetorheological damper is capable of adjusting the impedance of the controllable damping unit by controlling the current of the magnetorheological damper.

According to an example embodiment of the present application, the magnetorheological rotary brake performs a rotational motion, and the damping torque of the magnetorheological rotary brake is controlled by adjusting the current of the magnetorheological rotary brake.

According to an example embodiment of the present application, the magnetorheological damper performs a linear motion, and the output damping force of the magnetorheological damper is controlled by adjusting the current of the magnetorheological damper.

According to an example embodiment of the present application, the controllable damping unit comprises a hydraulic cylinder, a hydraulic valve, and a slider-crank mechanism, and the impedance of the controllable damping unit is controlled by adjusting the hydraulic valve.

According to an example embodiment of the present application, the controllable damping unit is configured in parallel with the elastic energy storage unit.

According to another aspect of the present application, this invention discloses a method of control of a knee joint, the method comprises: detecting the motion of the knee joint based on the signals of sensors; and then generating control signals for the elastic energy storage unit and the motor drive unit and/or the controllable damping unit, wherein the motor drive unit works as an actuator and generator in different states, the elastic energy storage unit is used for storing and releasing energy, and the controllable damping unit is used for providing an adjustable damping force/torque; wherein the elastic energy storage unit is used to store and release energy, and a power supply is used to store the electricity recovered by the motor driving unit and to power the motor driving unit, the elastic energy storage unit, sensors, and the controller.

According to yet another aspect of the present application, this invention discloses a walking assistance device comprising a smart knee joint as described above.

BRIEF DESCRIPTION OF DRAWINGS

The principles of the concepts of the present application are explained below by describing non-limiting embodiments of the present application with reference to the accompanying drawings. It is to be understood that the drawings are intended to illustrate example embodiments of the present application and are not intended to limit the same. The drawings are included to provide a further understanding of the inventive concept herein and are incorporated in and constitute a part of this specification. Like reference numerals in the drawings indicate like features. Wherein.

DETAILED DESCRIPTION OF EMBODIMENTS

Figure 1:
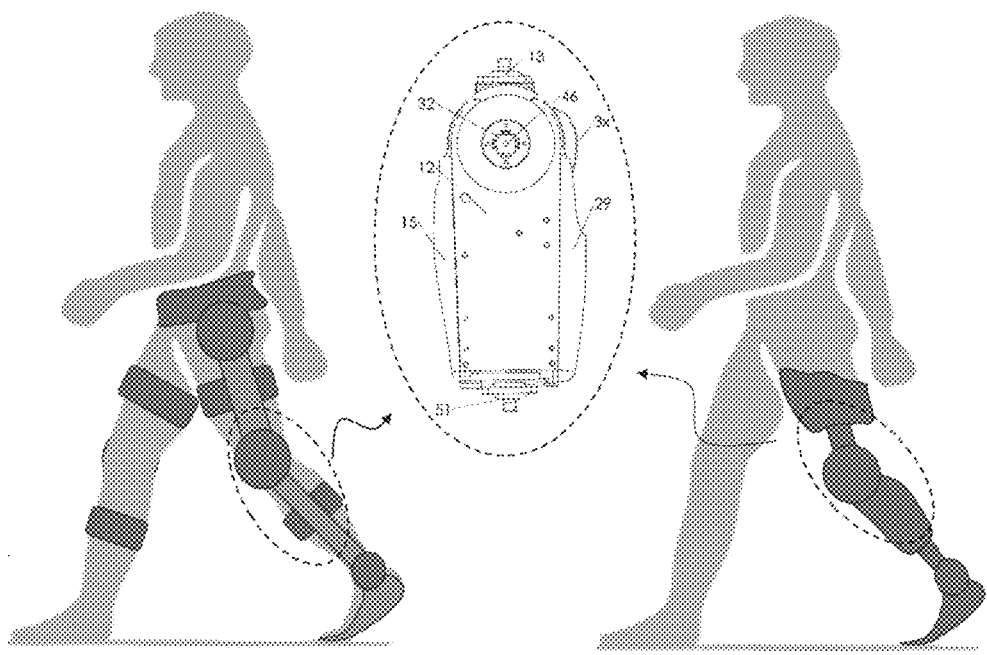
FIG. 1 shows a smart knee joint of an example embodiment of the present application.

For a better understanding of the present application, various aspects of the present application will be described in more detail below with reference to the example embodiments shown in the drawings. It is to be understood that these detailed descriptions are merely illustrative of example embodiments of the present application and are not intended to limit the scope of the present application in any way. Throughout the specification, like reference numerals refer to like elements. The expression "and/or" comprises any and all combinations of one or more of the associated listed items.

It should be noted that in this specification and in the claims, the expressions of first, second, etc., are used only to distinguish one feature from another, and are not intended to imply any limitation on the feature. Thus, the first rotor, first channel discussed herein may also be referred to as a second rotor, second channel, and vice versa, without departing from the teachings of the present application.

In the drawings, the thickness, size and shape of the components have been slightly exaggerated for ease of illustration. Accordingly, the drawings are by way of example only and not strictly to scale.

It should be understood that the expressions "comprising", "including" and/or "having", when used in this specification, indicate the existence of the listed features, elements, components and/or steps, but do not exclude the existence or addition of one or more other features, elements, components, steps and/or combinations thereof. In addition, when, for example, the expression "at least one of" appears before a list of listed features, modifies the entire listed feature, rather than modifying the individual elements in the list. In addition, when describing embodiments of the present application, "may" is used to mean "one or more embodiments of the present application". Also, the expression "example" is intended to refer to an example of the embodiments or exemplify embodiments.

Unless defined otherwise, all terms, comprising technical and scientific terms, used herein have the same meaning as commonly understood by one of ordinary skill in the art to which this application belongs. It is also to be understood that terms, such as those defined in commonly used dictionaries, are to be interpreted as having a meaning consistent with their meaning in the context of the related art and will not be interpreted in an idealized or overly formal sense unless expressly so defined herein.

Various aspects of the present application are described in more detail below with reference to the drawings, but the embodiments of the present application are not limited thereto.

Figure 2:
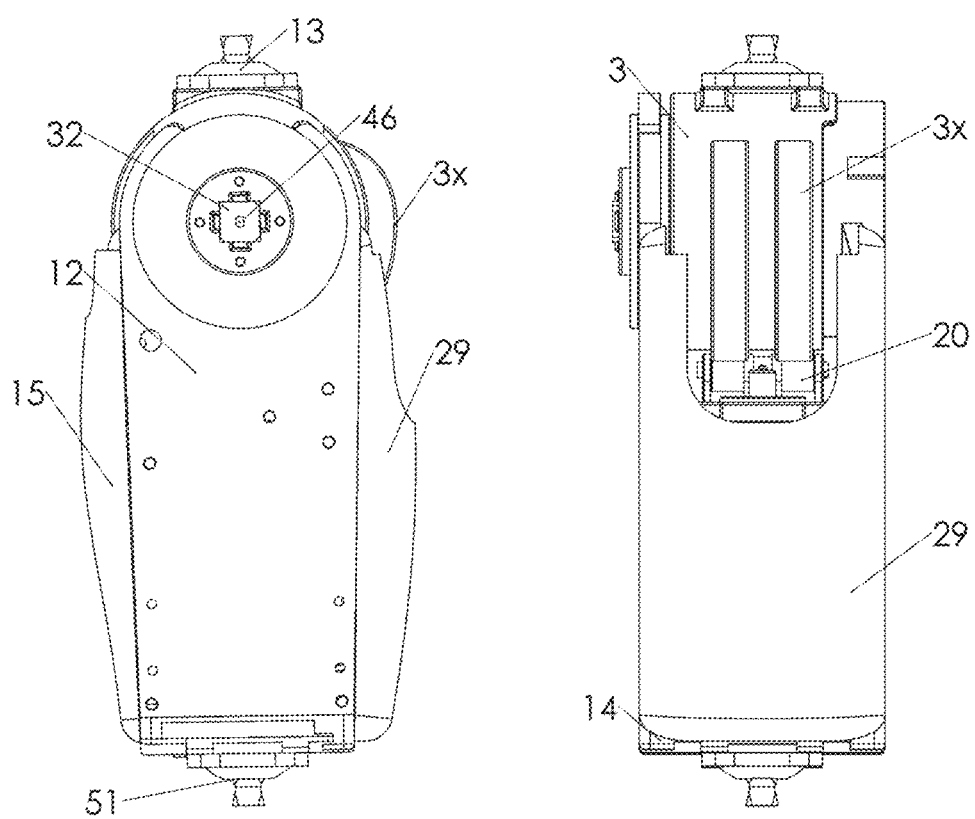
FIG. 2 shows a front view and a left view of a smart knee joint of an example embodiment of the present application.
Figure 3:
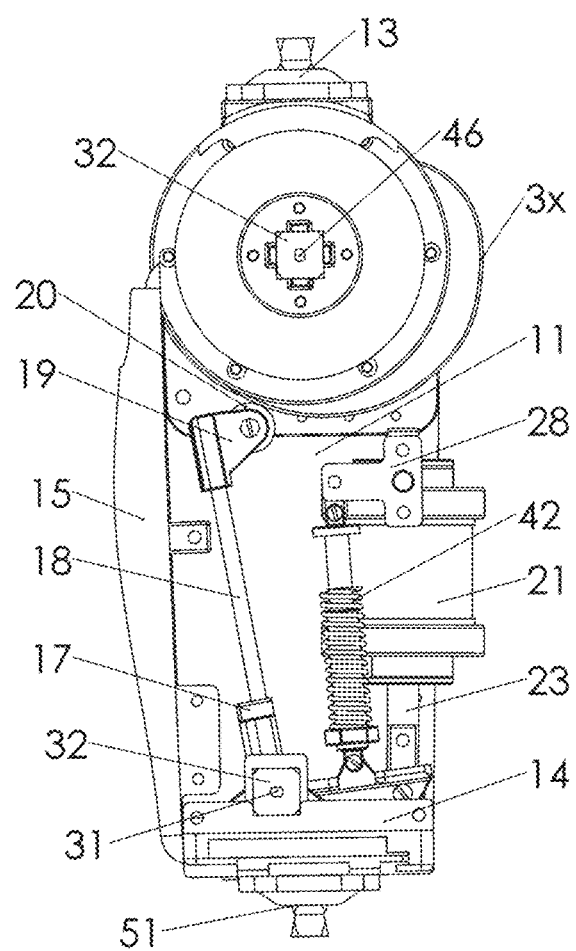
FIG. 3 shows details of components of an interior portion of a smart knee joint of an example embodiment of the present application.
Figure 4:
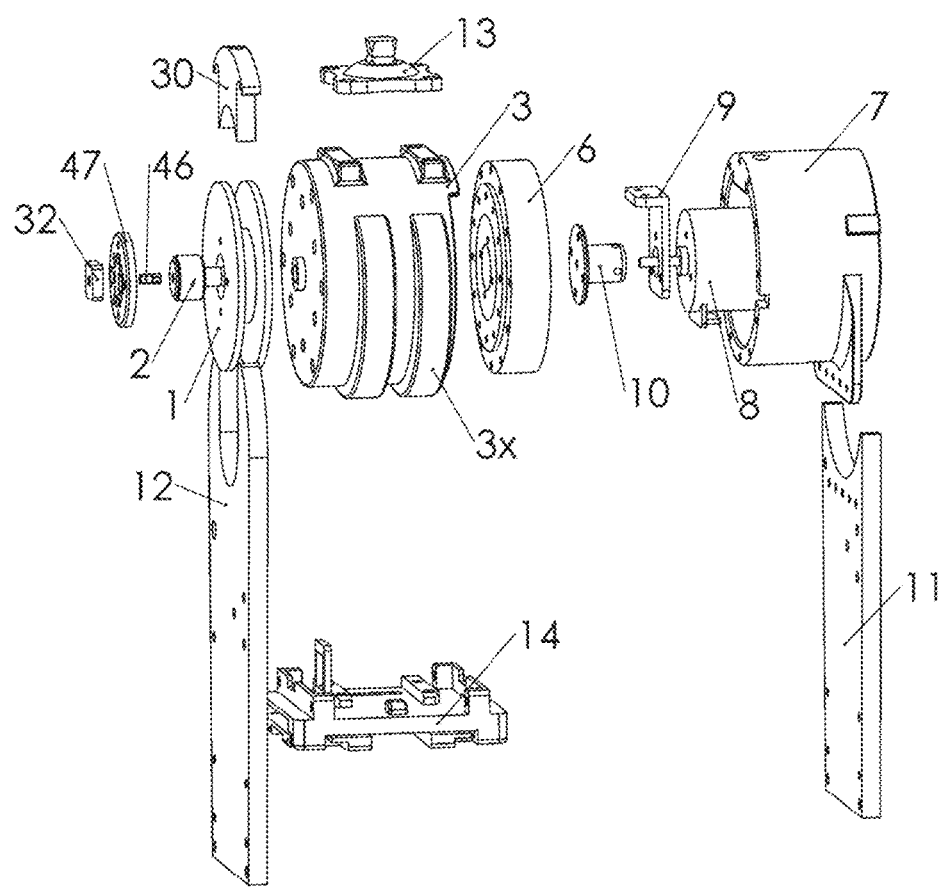
FIG. 4 is a perspective exploded view of a motor drive unit of a smart knee joint of an example embodiment of the present application.

FIG. 1 shows a smart knee joint according to an example embodiment of the present application. FIGS. 2-4 show a smart knee joint according to an example embodiment of the present application. As shown in FIG. 4, in this embodiment, a DC motor 8 is mounted on mounting bracket 9 that is fixed to a motor sleeve 7. The motor sleeve 7 is attached to a right bracket 11. The output shaft of the DC motor 8 is coupled to the input shaft of a harmonic gear 6 through a coupling 10, and the output shaft of the harmonic gear 6 is coupled to a knee joint housing 3.

The knee joint housing 3 is mounted on a shaft of a bearing 2 which is mounted on a fixing member 1. The fixing member 1 is fixed to a left bracket 12. The right bracket 11 and the left bracket 12 are both mounted on a bottom fixing member 14. A thigh adaptor 13 is mounted on the knee joint housing 3, and a shank adaptor 51 is mounted on the bottom fixing member 14. A cam 3x is mounted on the knee joint housing 3. The shell of a knee angle sensor 32 is fixed to the fixing member 1 through a sensor fixing member 47, and the input shaft of the knee angle sensor 32 is connected to the shaft of the bearing 2 through a connecting shaft 46. The knee angle sensor 32 is used to measure the rotation angle between the knee joint housing 3 and the left bracket 12.

A turret 17 is mounted on the bottom fixing member 14 and is rotatable about a rotating shaft 31. An angle sensor 32 is employed to measure the rotation angle between turret 17 and the bottom fixing member 14. One end of a leaf spring 18 is mounted on the left end of turret 17, and the other end of the leaf spring 18 is mounted with a follower bracket 19. A follower 20 is rotatable about a fixed axis on the follower bracket 19 while in contact with the cam 3x.

A magnetorheological damper comprises a piston connecting shaft 23, a piston, and a housing 21. The piston connecting shaft 23 of the magnetorheological damper is connected to the right end of the turret 17 by a hinge, and a housing 21 of the magnetorheological damper is hinged to a damper holder 28, and the damper holder 28 is mounted on the left bracket 12. Two restoring springs 42 are mounted in parallel with the magnetorheological damper for resetting the magnetorheological damper to its original position when the external load is removed.

Figure 5:
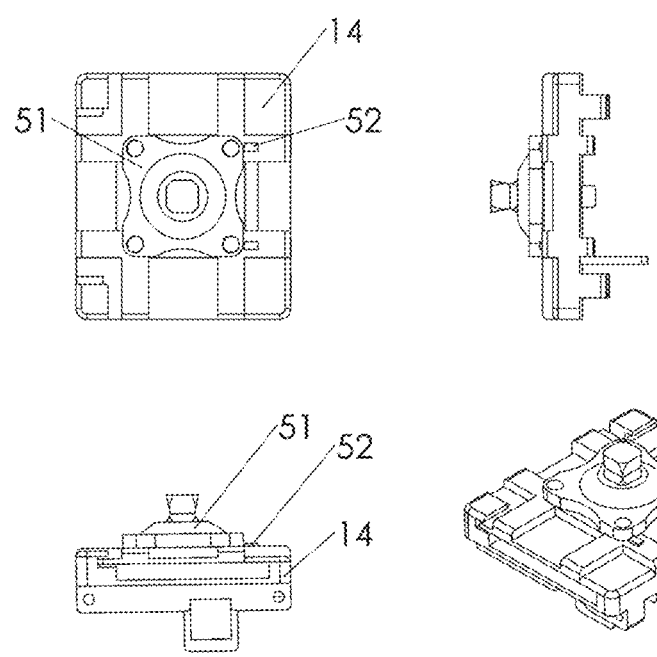
FIG. 5 shows a custom-made axial force measurement device for a smart knee joint of an example embodiment of the present application.

FIG. 5 shows a custom-made axial force measurement device for a smart knee joint according to an example embodiment of the present application. The bottom fixing member 14 is equipped with a cantilever beam structure, and a shank adaptor 51 is mounted on the cantilever beam. A strain gauge 52 is mounted at the fixed end of the cantilever beam. The cantilever beam is deformed when an axial force load is applied to the shank adaptor 51. Because of that, the resistance of the strain gauge 52 is changed accordingly. The magnitude of the axial force load can be calculated based on the change of the resistance. It is noted that, to avoid breaking the strain gauge 52, the maximum deformation of the cantilever beam is limited by two blocks.

Figure 6:
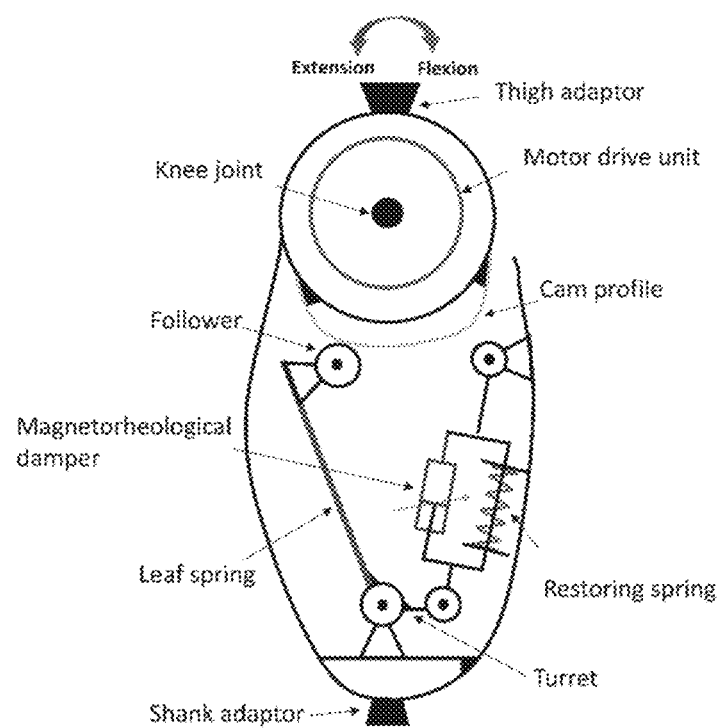
FIG. 6 shows a schematic diagram of a smart knee joint of an example embodiment of the present application, wherein the smart knee joint employing a motor driving unit.

FIG. 6 shows a schematic diagram of a smart knee joint comprising a motor driving unit according to an example embodiment of the present application. The motor driving unit can be used as an actuator to provide driving force or can be used as a generator to harvest energy by converting the mechanical negative energy into electricity. When the knee joint flexes and extends, the cam will perform a rotary motion to push the follower.

When the magnetorheological damper is powered to be locked, the turret is fixed. The leaf spring will be deformed by the cam, thereby generating a bias torque for the knee joint.

When the magnetorheological damper is powered off, the turret will rotate freely, and the leaf spring will not be deformed.

When the magnetorheological damper is powered on but there is a relative motion between the damper piston and the damper housing, the turret will rotate. The leaf spring will be deformed by the cam thus generating a bias torque for the knee joint. It is noteworthy that in this case, the magnetorheological damper will dissipate mechanical energy.

Figure 7:
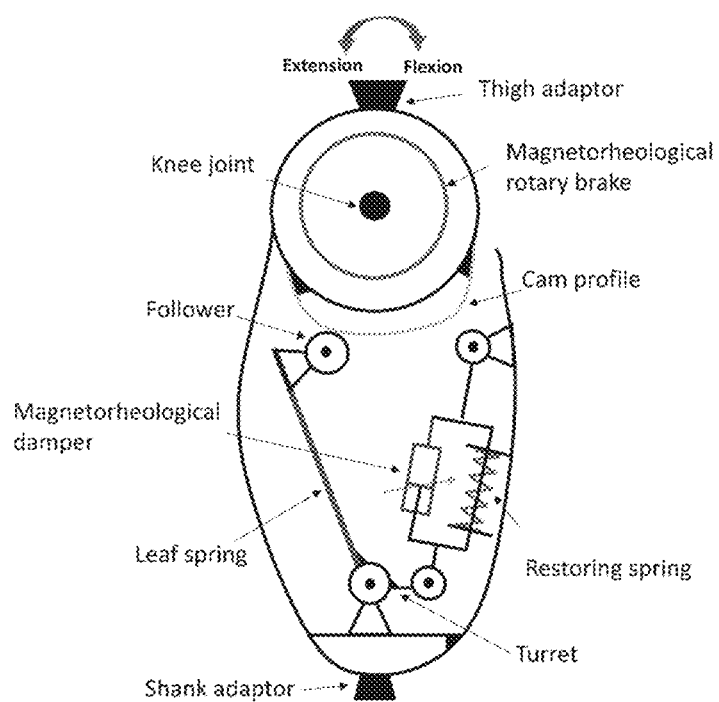
FIG. 7 shows a schematic diagram of a smart knee joint of an example embodiment of the present application, wherein the smart knee joint comprising a controllable damping unit—a magnetorheological rotary brake.

FIG. 7 shows a schematic diagram of a smart knee joint according to an example embodiment of the present application, and the smart knee joint employs a magnetorheological rotary brake. The magnetorheological rotary brake regulates its impedance torque by controlling its current. When the knee joint flexes and extends, the cam will rotate to push the follower.

When the magnetorheological damper is powered to be locked, the turret is fixed. The leaf spring will be deformed by the cam, thereby providing a biasing torque for the knee joint.

When the magnetorheological damper is powered off, the turret will rotate freely and the leaf spring will not be compressed.

When the magnetorheological damper is powered on but there is a relative motion between the damper piston and the damper housing, the turret will rotate. The leaf spring will be deformed by the cam thus generating a bias torque for the knee joint. It is noted that the magnetorheological damper will dissipate mechanical energy.

Figure 8:
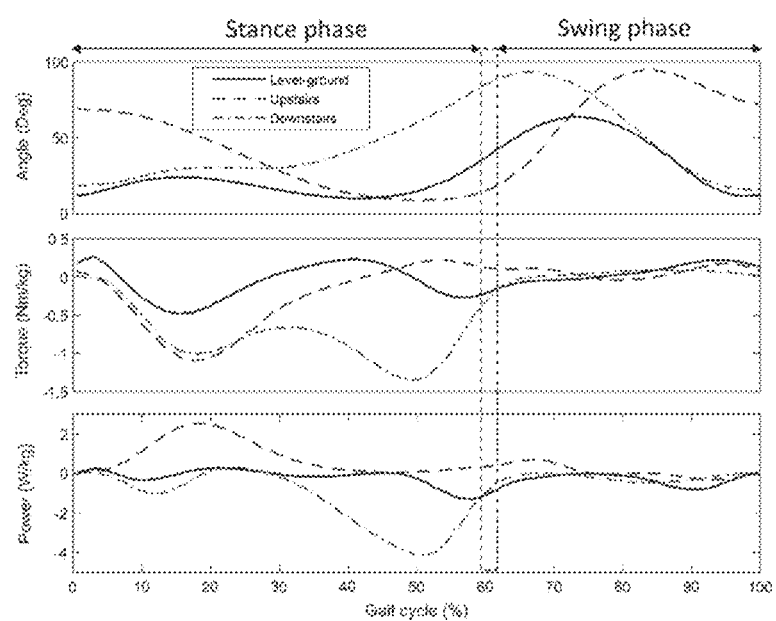
FIG. 8 shows angle curves, torque curves and power curves of a human knee joint during one cycle of level-ground walking, stairs ascending, and stairs descending.
Figure 9:
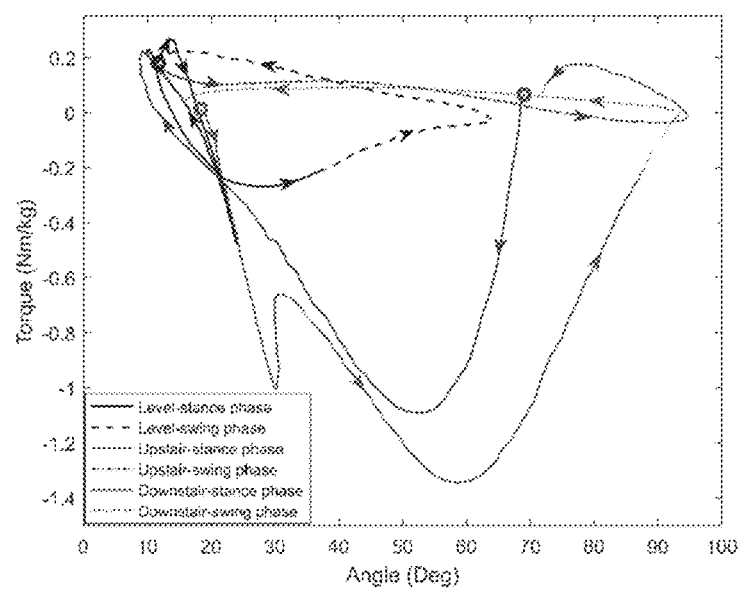
FIG. 9 shows torque-angle curves of a human knee joint during level-ground walking, stairs ascending, and stairs descending.

FIG. 8 shows angle curves, torque curves, and power curves of a human knee joint during one gait cycle of level-ground walking, stairs ascending, and stairs descending. The stance phase and swing phase are both indicated in this figure. FIG. 9 shows torque-angle curves of a human knee joint during level-ground walking, stairs ascending, and stairs descending. In FIGS. 8 and 9, the solid line represents the stance phase and the dashed line refers to the swing phase.

Figure 10:
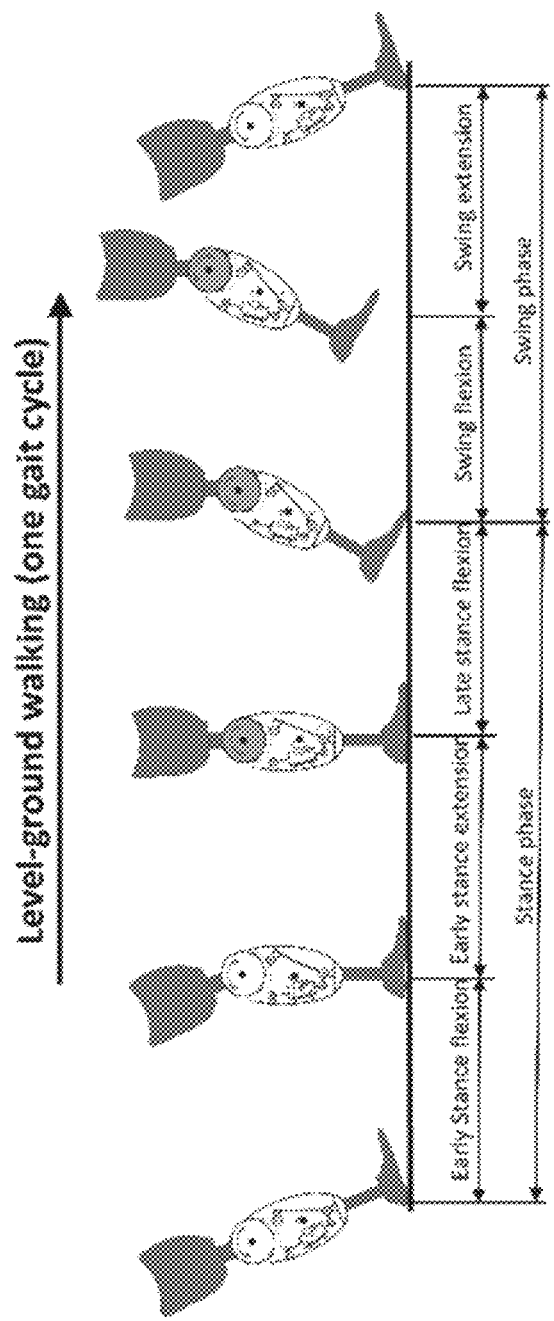
FIG. 10 shows working principles of a smart knee joint comprising a motor drive unit, an elastic energy storage unit, and a magnetorheological damper during level-ground walking of an example embodiment of the present application.

FIG. 10 shows the working principles of a smart knee joint during level-ground walking according to an example embodiment of the present application. In the early stance flexion and extension phases, the magnetorheological damper is powered on to be locked and the leaf spring is deformed by the cam so as to store and release mechanical energy. A bias torque is generated by the leaf spring to support the body weight in these phases. In addition, in these phases, the DC motor is powered off.

In the late stance flexion phase, the magnetorheological damper is powered off and the leaf spring is free to rotate. The DC motor is used as a generator to harvest energy at the same time provide a controllable damping torque. Besides, in this phase, the magnetorheological damper also can be powered on to adjust the damping force, and there is a relative motion between the damper piston and the damper housing. In this case, the leaf spring is deformed by the cam to provide a bias torque for the knee joint.

During the stance phase of the level-ground walking, the knee joint will mimic the torque-angle curve (solid line)

shown in FIG. 9. During the swing phase of the level-ground walking, the knee joint will track the angle curve of level-ground walking shown in FIG. 8. The knee joint can mimic the mentioned level-ground torque-angle curve or track the angle curve by controlling the DC motor and the magnetorheological damper.

Figure 11:
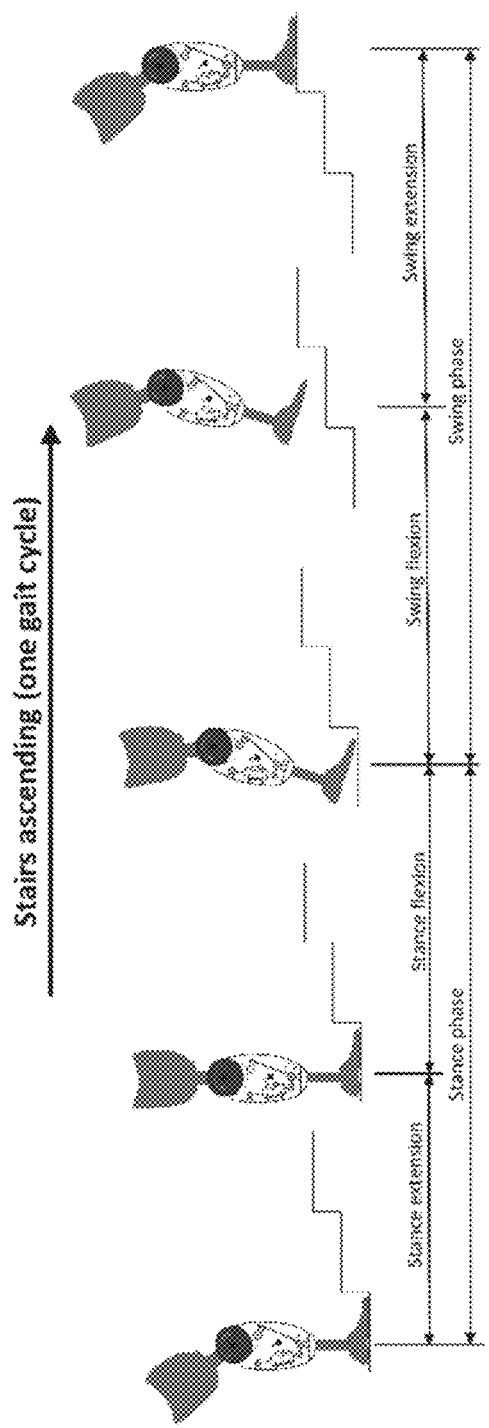
FIG. 11 shows working principles of a smart knee comprising a motor drive unit, an elastic energy storage unit, and a magnetorheological damper during stairs ascending of an example embodiment of the present application.

FIG. 11 shows the working principles of a smart knee joint during upstairs walking according to an example embodiment of the present application. As the power of the knee joint is positive power throughout the gait cycle, as shown in FIG. 8, the DC motor is always used as an actuator to provide the driving force.

In addition, during the whole gait cycle of the upstairs walking, the magnetorheological damper is powered off and the leaf spring is free to rotate. In the stance phase of upstairs walking, the knee joint will mimic the upstairs walking torque-angle curve (solid line) shown in FIG. 9. During the swing phase of upstairs walking, the knee joint will perform the angle tracking of the upstairs walking shown in FIG. 8. The knee joint can track the upstairs walking torque-angle curve and angle curve by controlling the DC motor throughout the whole gait cycle.

Figure 12:
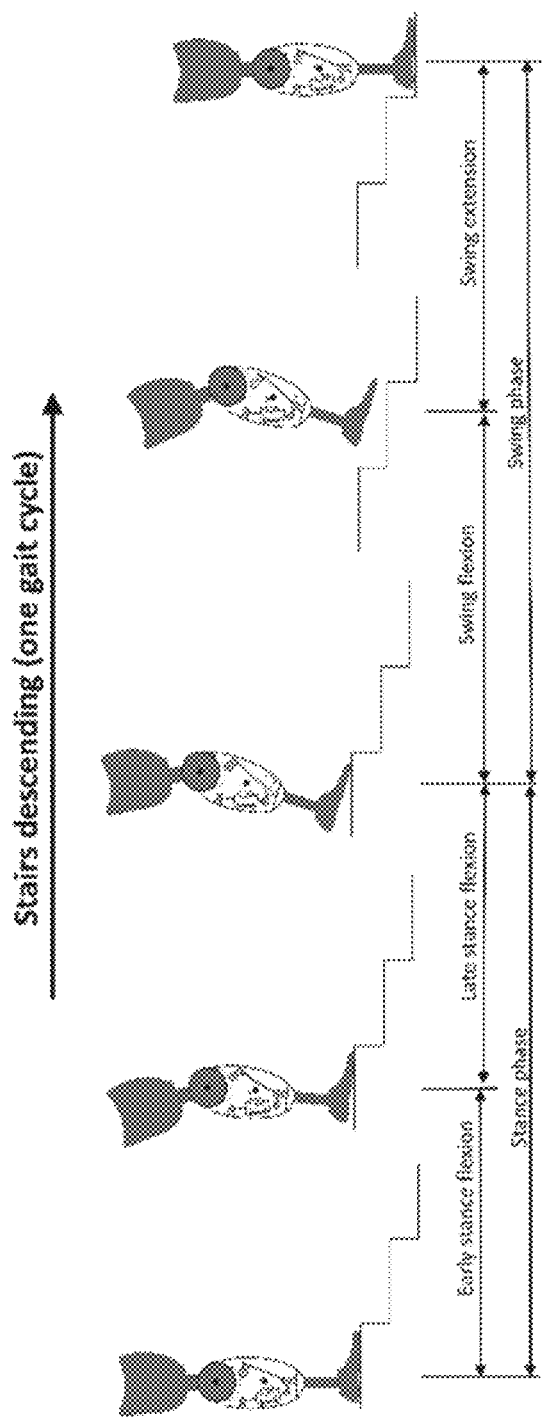
FIG. 12 shows the working principles of a smart knee joint comprising a motor drive unit, an elastic energy storage unit, and a magnetorheological damper during stairs descending of an example embodiment of the present application.

FIG. 12 shows the working principles of a smart knee joint during downstairs walking according to an example embodiment of the present application. In the early stance flexion phase, the magnetorheological damper is powered on to be locked and the leaf spring is deformed by the cam to provide a bias torque to support the bodyweight of the amputees. Mechanical energy has been stored in the leaf spring. Then in the late stance flexion phase, the magnetorheological damper is also powered on, but there is a relative motion between the damper piston and damper housing. The elastic energy stored in the leaf spring will be dissipated by the magnetorheological damper. Besides, the bias torque from the leaf spring will be gradually decreased.

During the swing phase of downstairs walking, the magnetorheological damper is powered off and the leaf spring is free to rotate. During the whole gait cycle, as the work of the knee joint is negative, the DC motor can be used as a generator to harvest the negative mechanical energy so as to extend the working time of the knee joint.

During the stance phase of downstairs walking, the knee joint will mimic the downstairs walking torque-angle curve (solid line) shown in FIG. 9. During the swing phase of downstairs walking, the knee joint will track the downstairs walking angle curve shown in FIG. 8. The knee joint can reproduce downstairs walking torque-angle curve and angle curve by controlling the DC motor current and the magnetorheological damper current.

It should be noted that during the uphill and downhill, the kinematics and kinetics of the human knee are close to those of level-ground walking. Given that, the working principles of the smart knee joint during uphill and downhill are close to that during level-ground walking. However, the torque-angle curve and angle curve should be adjusted accordingly.

Figure 13:
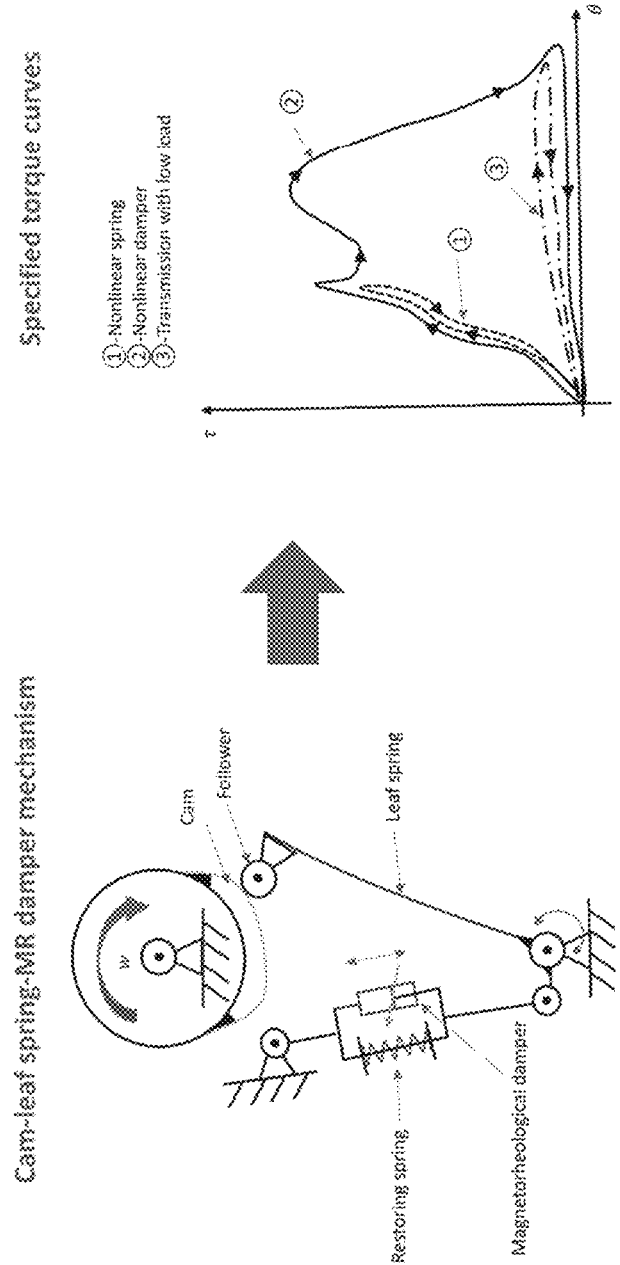
FIG. 13 shows a schematic diagram of a cam-leaf spring-magnetorheological damper mechanism and three torque-angle curves corresponding to three working modes.

FIG. 13 shows a schematic diagram of a cam-leaf spring-magnetorheological damper device and the torque-angle curve outputs corresponding to three working modes. By controlling the magnetorheological damper, the cam-leaf spring-magnetorheological damper device can be used as a non-linear spring mechanism for storing and releasing mechanical energy (①); also may be used as a Non-linear damper for dissipating mechanical energy (②); or a transmission with low load (③). The low load results from the damping force of the magnetorheological damper.

Although some embodiments of the present application have been described, those skilled in the art can make variations or modifications to these embodiments upon knowing the basic inventive concept. Although details of the embodiments are described, it is understood that it is not necessary to include all elements in the described embodiments. Instead, some elements in the embodiments could be omitted or altered, without departing from the invention. The appended claims are intended to be considered as comprising the described embodiments and all the variations or modifications fall into the scope of the present application.

What is claimed is:

1. A smart knee joint for a human lower limb exoskeleton, a prosthesis, and an orthosis, attached to a knee joint, comprising:
   1) a motor driving unit or a controllable damping unit, the motor driving unit including a motor and a transmission, and having two working modes: a generator mode and an actuator mode, the motor driving unit being adjusted to a corresponding working mode based on states and walking modes of the knee joint;
   2) an elastic energy storage unit including an elastic element, a transmission, and a working mode regulator, the elastic energy storage unit having three working modes: being locked mode, free mode, and energy dissipation mode, the elastic energy storage unit being adjusted to a corresponding working mode based on states and walking modes of the knee joint, wherein the working mode regulator comprises a magnetorheological damper and a restoring spring;
   3) sensors for detecting the motion of the knee joint;
   4) a controller for monitoring the states and the walking modes of the knee joint in real-time based on signals of the sensors, and generating control signals for the elastic energy storage unit and the motor driving unit or the controllable damping unit;
   5) a power supply for powering the motor driving unit, the controllable damping unit, the elastic energy storage unit, the sensors, and the controller, and storing electric energy recovered by the motor, the power supply being one or both of a battery and a supercapacitor; and
   6) connecting devices comprising a thigh connecting device and a shank connecting device.

2. The smart knee joint of claim 1, wherein the motor driving unit comprises a motor, a gear reduction box, and a bevel gear transmission.

3. A smart knee joint of claim 1, wherein the motor driving unit comprises a motor and a harmonic gear transmission.

4. The smart knee joint of claim 1, wherein the motor driving unit comprises a motor, a gear transmission, a ball-screw transmission, and a slider-crank mechanism.

5. The smart knee joint of claim 1, wherein the motor driving unit comprises a motor, a timing-belt transmission, a ball-screw transmission, and a slider-crank mechanism.

6. The smart knee joint of claim 1, wherein the elastic energy storage unit is configured in parallel with the motor driving unit.

7. The smart knee joint of claim 1, wherein the elastic element, the transmission, and the working mode regulator are arranged in series.

8. The smart knee joint of claim 1, wherein the elastic element in the elastic energy storage unit is one or more of a coil spring, a leaf spring, a gas spring, and a rubber spring.

9. The smart knee joint of claim 1, wherein the transmission in the elastic energy storage unit is one or more of a pulley rope mechanism, a slider-crank mechanism, and a cam mechanism.

10. The smart knee joint of claim 9, wherein a cam profile of the cam is arranged to satisfy a specific elastic torque-angle curve.

11. The smart knee joint of claim 1, wherein when the elastic energy storage unit operates in the being locked mode, the magnetorheological damper in the working mode regulator is energized to be locked.

12. The smart knee joint of claim 1, wherein the magnetorheological damper in the working mode regulator is de-energized when the elastic energy storage unit is operating in the free mode.

13. The smart knee joint of claim 1, wherein when the elastic energy storage unit operates in the energy dissipation mode, the magnetorheological damper in the working mode regulator is energized, but there is a relative motion between a damper piston and a damper housing, a damping force is regulated by adjusting the current applied to the magnetorheological damper.

14. The smart knee joint of claim 1, wherein the sensors comprise one or more of an axial force sensor, a torque sensor, a knee angle sensor, an inertial measurement unit for measuring the motion of the thigh, an inertial measurement unit for measuring the motion of the shank, and electromyographic signal sensors.

15. The smart knee joint of claim 1, wherein the controller detects the motion states and the walking modes of the knee joint based on the signals of the sensors, and generates one or both of a reference angle or a reference torque for the motor driving unit.

16. The smart knee joint of claim 1, wherein the knee joint is enabled to fully or partially reproduce the biomechanics of the human knee joint by controlling the motor driving unit, the controllable damping unit, and the elastic energy storage unit.

17. The smart knee joint of claim 16, wherein the biomechanics of the human knee joint is a torque-angle curve during the stance phase and an angle curve during the swing phase.

18. The smart knee joint of claim 1, wherein the controllable damping unit is a magnetorheological rotary brake capable of adjusting an impedance torque of the controllable damping unit by controlling the current applied to the magnetorheological rotary brake.

19. The smart knee joint of claim 1, wherein the controllable damping unit comprises a magnetorheological damper and a slider-crank mechanism, and the magnetorheological damper is capable of adjusting an impedance torque of the controllable damping unit by controlling the current applied to the magnetorheological damper.

20. The smart knee joint of claim 1, wherein the controllable damping unit comprises a hydraulic cylinder, a hydraulic valve, and a slider-crank mechanism, and an impedance torque of the controllable damping unit is controlled by adjusting the hydraulic valve.

21. The smart knee joint of claim 1, wherein the controllable damping unit is connected in parallel with the elastic energy storage unit.

22. A method of control of a knee joint, comprising:
detecting motion of the knee joint by sensors included in a smart knee joint for a human lower limb exoskeleton, a prosthesis, and an orthosis, the smart knee joint being attached to the knee joint and comprising an elastic energy storage unit, and a motor drive unit or a controllable damping unit; and providing control signals for the elastic energy storage unit and the motor drive unit or the controllable damping unit based on the signals of the sensors, wherein the motor drive unit includes a motor and a transmission, and has two working modes: a generator mode and an actuator mode, the motor drive unit being adjusted to a corresponding working mode based on states and walking modes of the knee joint, wherein the elastic energy storage unit includes an elastic element, a transmission, and a working mode regulator, the elastic energy storage unit having three working modes: being locked mode, free mode, and energy dissipation mode, and the elastic energy storage unit being adjusted to a corresponding working mode based on the states and the walking modes of the knee joint, wherein the working mode regulator comprises a magnetorheological damper and a restoring spring;

wherein the control signals are generated by a controller included in the smart knee joint, and the controller is configured for monitoring the states and the walking modes of the knee joint in real-time based on the signals of the sensors, and generating the control signals for the elastic energy storage unit, and the motor drive unit or the controllable damping unit;

wherein the smart knee joint further comprises: a power supply for powering the motor drive unit, the controllable damping unit, the elastic energy storage unit, the sensors, and the controller, and storing electric energy recovered by the motor, the power supply being one or both of a battery and a supercapacitor; and connecting devices comprising a thigh connecting device and a shank connecting device.

23. An apparatus for assisting walking, comprising a smart knee joint,
wherein the smart knee joint comprises:
1) a motor driving unit or a controllable damping unit, the motor driving unit including a motor and a transmission, and having two working modes: a generator mode and an actuator mode, the motor driving unit being adjusted to a corresponding working mode based on states and walking modes of the knee joint;
2) an elastic energy storage unit including an elastic element, a transmission, and a working mode regulator, the elastic energy storage unit having three working modes: being locked mode, free mode, and energy dissipation mode, the elastic energy storage unit being adjusted to a corresponding working mode based on states and walking modes of the knee joint, wherein the working mode regulator comprises a magnetorheological damper and a restoring spring;
3) sensors for detecting the motion of the knee joint;
4) a controller for monitoring the states and the walking modes of the knee joint in real-time based on signals of the sensors, and generating control signals for the elastic energy storage unit and the motor driving unit or the controllable damping unit;
5) a power supply for powering the motor driving unit, the controllable damping unit, the elastic energy storage unit, the sensors, and the controller, and storing electric energy recovered by the motor, the power supply being one or both of a battery and a supercapacitor; and
6) connecting devices comprising a thigh connecting device and a shank connecting device.

* * * * *